United States Patent [19]

Nishio et al.

[11] Patent Number: 5,132,919
[45] Date of Patent: Jul. 21, 1992

[54] AUTOMATIC MEASURING DEVICE FOR MEASURING THE AMOUNT OF WAX, OIL AND OTHER SUBSTANCES APPLIED ON THE SURFACE OF A WORKPIECE

[75] Inventors: Masahiro Nishio, Tajimi; Masaya Imai, Konan; Mitsuo Kamio; Hiroyuki Shindo, both of Toyoake; Sadao Hisada, Nagoya; Atsuo Watanabe; Shigeru Kato, both of Hino, all of Japan

[73] Assignees: Sumitomo Light Metal Industries, Limited; Fuji Electric Co., Limited, Japan

[21] Appl. No.: 615,594

[22] Filed: Nov. 19, 1990

[30] Foreign Application Priority Data

Nov. 20, 1989 [JP] Japan ................................. 1-301408

[51] Int. Cl.$^5$ ............................................. G01N 21/00
[52] U.S. Cl. ................................ 364/551.01; 364/580
[58] Field of Search ................... 364/550, 551.01, 552, 364/555, 579, 580, 478, 570, 571.01, 468, 469, 472, 502; 73/864.81, 864.82, 864.83; 134/40

Primary Examiner—Parshotam S. Lall
Assistant Examiner—Michael Zanelli
Attorney, Agent, or Firm—Davis, Bujold & Streck

[57] ABSTRACT

This invention provides automatic measuring apparatus for measuring the amount of wax, oil and other substances applied on a specified portion of a workpiece. A controller unit controls cleaning, measuring and calculating operations. Under such control, the workpiece set in a cleaning device is automatically cleaned using an appropriate solvent. The solvent used for cleaning the workpiece is automatically supplied to a measuring device and the absorption spectrum of the solvent is measured. Based on the data of the absorption spectrum measured by the measuring device, a calculating device automatically calculates the application amount of the wax, the oil or the other substances applied over the workpiece. The automatic measuring apparatus thus enhances measuring precision and reduces the time period required for the measuring operation. During the cleaning operation prior to the measuring operation, the solvent is sealed and prevented from leaking in the cleaning device, thereby assuring a safe operating environment.

24 Claims, 4 Drawing Sheets

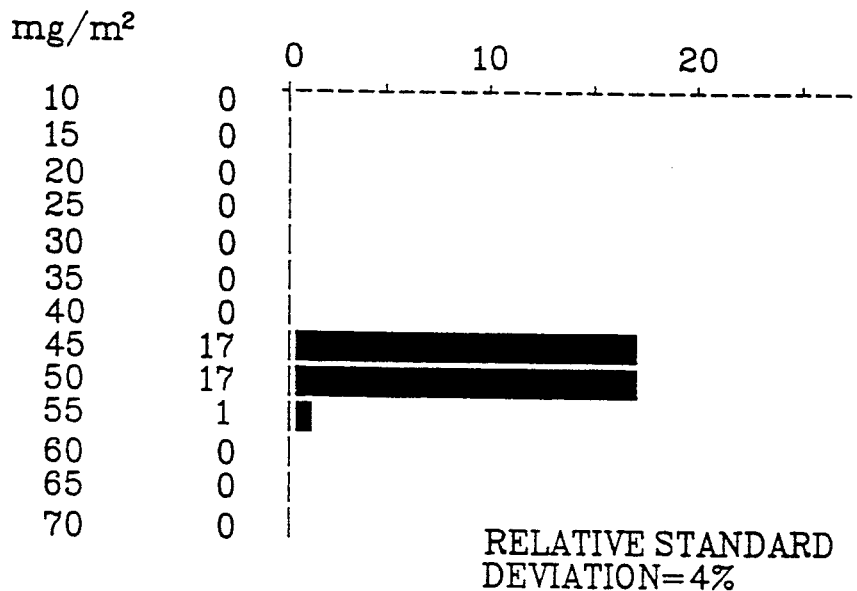
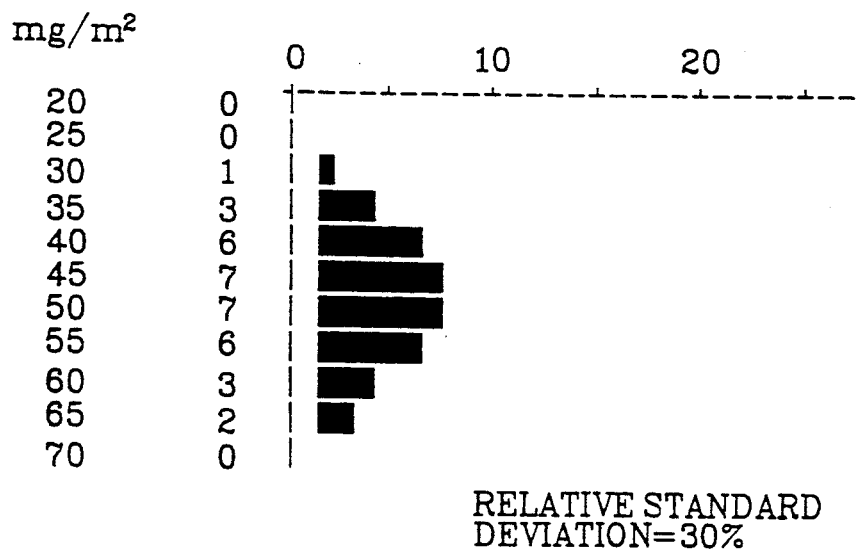

AUTOMATIC MEASURING DEVICE FOR MEASURING THE AMOUNT OF WAX, OIL AND OTHER SUBSTANCES APPLIED ON THE SURFACE OF A WORKPIECE

BACKGROUND OF THE INVENTION

This invention relates to an automatic measuring device that measures the application amount of wax, oil and other substances over the coated surface of a paint-coated plate.

The measuring of the amount of wax applied over the coated surface of a paint-coated plate consisting of sheets, coils and other materials by quantitative analysis is known in the art. In this method, after measuring the weight of the paint-coated plate, the wax is washed away from the coated surface of the plate using hot water, organic solvent and the like. The washed plate is dried, cooled, and measured again. The amount of wax is calculated according to the difference between the weight of the paint-coated plate prior to washing and after washing.

In another known method, a given area is cut out from the paint-coated plate. The wax applied over the coated surface of the cut-out area of the paint-coated plate is dissolved in carbon tetrachloride, hexane, or other organic solvent that does not erode the coated surface of the cut-out area of the paint-coated plate. Subsequently, the solvent is measured through infrared spectroscopic analysis, gas chromatography, or other known methods to obtain the amount of wax applied over the coated surface of the cut-out area of the paint-coated plate.

By the first-mentioned quantitative analysis, an amount as small as 0.Xmg of substances is measured; and, in which measuring errors are caused by changes in the temperature and humidity of the measuring room, in the temperature of the paint-coated plate, and other conditions. Measuring precision is thus impaired. Moreover, an operator who performs the measuring operation should be trained well. The measuring operation requires a number of intricate process steps including first, weighing, washing, drying, cooling; second, weighing, calculating, and other steps. Therefore, as a negative feature, the measuring operation takes a long time and is difficult to mechanize.

In the second mentioned method, the measuring operation consists of dissolution and measurement. When gas chromatography is used, for example, the measuring operation takes five to ten minutes per workpiece. Thus, as a same negative feature as that of the first mentioned method, this method requires a long time.

Wherefore, an object of this invention is to provide an automatic measuring device for measuring the application amount of wax and other substances that can mechanize the measuring operation, enhance measuring precision, and reduce the time period required for the measuring operation.

Other objects and benefits of the invention will become apparent from the detailed description which follows hereinafter when taken in conjunction with the drawing figures which accompany it.

SUMMARY OF THE INVENTION

To solve this and other objects, this invention provides an automatic measuring device for measuring the amount of wax, oil and other substances applied on the surface of a sample. The device, as shown in FIG. 1, comprises a cleaning means M1 for cleaning a given portion of a sample set in the cleaning means M1 by using a predetermined amount of solvent and for dissolving the wax over the sample into the solvent, and a measuring means M2 for measuring the absorption spectrum of the solvent. The device also comprises a calculating means M3 for comparing measured spectrum data and a predetermined calibration data and calculating the application amount of the wax based on comparison results. The device further comprises an automatic control means M4 for controlling the cleaning means M1, the measuring means M2 and the calculating means M3.

Under the control of the automatic control means M4, the cleaning means M1 cleans the sample set therein with the predetermined amount of the solvent. The solvent is then supplied to the measuring means M2. The measuring means M2 measures the absorption spectrum of the solvent. Subsequently, the calculating means M3 calculates the application amount of the wax over the sample based on the measured spectrum data.

BRIEF DESCRIPTION OF THE DRAWINGS

FIG. 4 is a graph showing exemplary data measured through the measurement process steps of this invention as depicted in FIG. 3.

FIG. 5 is a graph showing exemplary data as obtained from a prior art measuring method.

DETAILED DESCRIPTION OF THE PREFERRED EMBODIMENT

Figure 1:
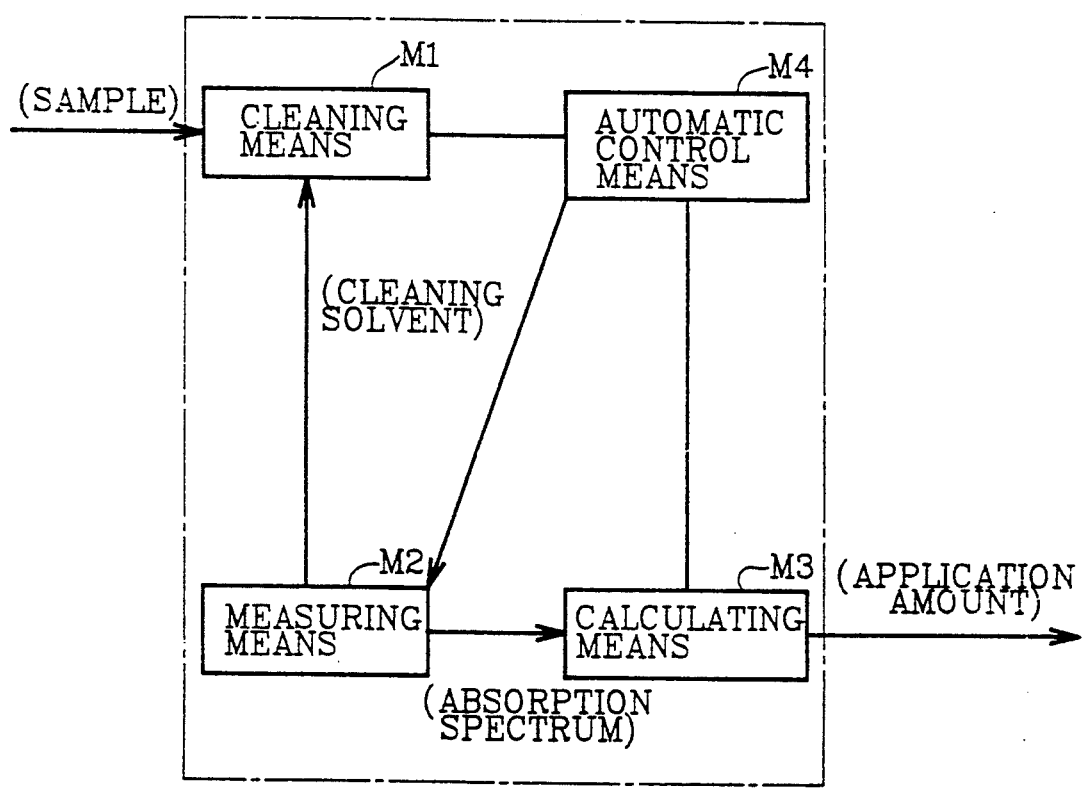
FIG. 1 is an illustration of a basic structure of the present invention.

A measuring arrangement according to the present invention will now be explained with particular reference to FIG. 2. A sample 1 is punched by a press 2 into a desired configuration from a paint-coated plate (not shown) with wax applied on its coated front and back surfaces. A robot 3 loads the sample 1 on a cassette 4, conveys the cassette 4 to an automatic cleaning cell 5 comprising the cleaning means M1, and moves the sample 1 from the cassette 4 into the automatic cleaning cell 5. The automatic cleaning cell 5 comprises a pair of cells 5a and 5b being movable and having hollows 5c and 5d therein, respectively. The hollows 5c and 5d of the cells 5a and 5b as well as the sample 1 set in the automatic cleaning cell 5 form front and back compartments 6 and 7 at opposite sides of the sample 1. The front and back compartments 6 and 7 are each at one end connected through piping 8 to a solvent tank 9 and at their other ends connected through piping 10 to an infrared spectroscope 11 comprising the measuring means M2.

A constant flow pump 12 is provided in-line with the piping 8. The piping 8 is connected via valves 13a and 13b having an air regulating mechanism to respective solvent inlets of the front and back compartments 6 and 7 of the automatic cleaning cell 5. On the other hand, the piping 10 is connected from respective solvent outlets of the front and back compartments 6 and 7 via valves 14a and 14b to the infrared spectroscope 11. The infrared spectroscope 11 is of a type well known to those skilled in the art and is a Fourier-transform infrared spectroscope having therein a flow cell 15, a light emitting section 15a, a detecting section 15b and associated sections. The flow cell 15 is connected at its inlet through the piping 10 to the front and back compartments 6 and 7 of the automatic cleaning cell 5 by opening the valves 14a and 14b, respectively. The flow cell 15 is connected at its outlet through the piping 16 to a drainage tank 17.

The infrared spectroscope 11 is connected to a computer 18 which comprises both the calculating means M3 and the automatic control means M4. The computer 18 is also connected to a CRT 19, a keyboard 20, a printer 21, a host computer 18a and associated components. The computer 18 controls the press 2, the robot 3, the automatic cleaning cell 5, the constant flow pump 12, the valves 13a, 13b, 14a, 14b, the infrared spectroscope 11 and associated components.

The robot 3, the cassette 4, the automatic cleaning cell 5, the solvent tank 9, the drainage tank 17 and associated components are preferably covered and sealed by a covering (indicated by the dashed box 22) having an openable lid (not shown) through which the sample 1 is delivered. Any vapor of volatile solvents is thus prevented from leaking outside.

Figure 2:
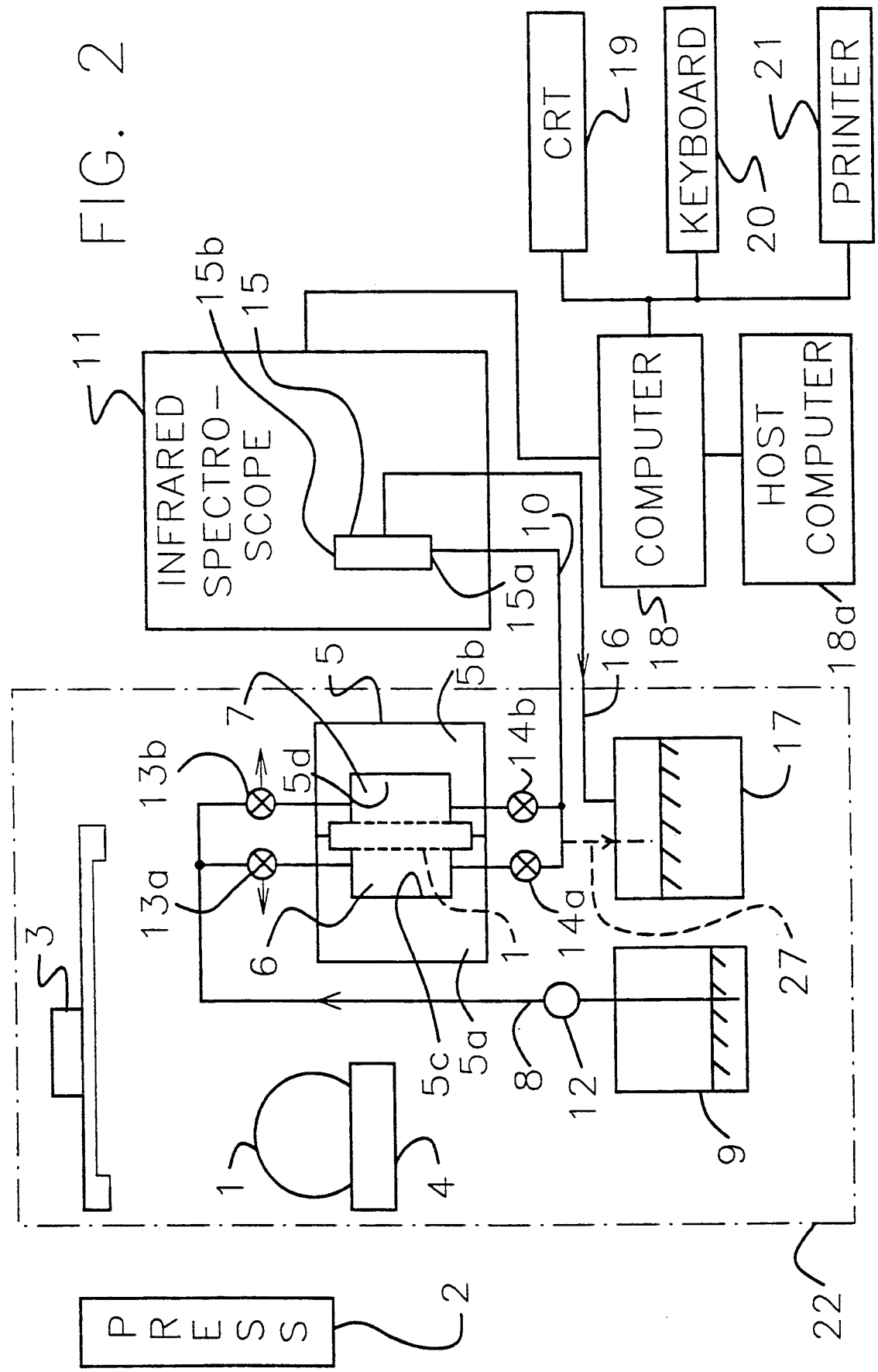
FIG. 2 is a block diagram of an automatic measuring device for obtaining the amount of wax, oil and other substances applied on the surface of a sample embodying the present invention.

To reduce the time period required for cleaning the sample 1 in the automatic cleaning cell 5, solvent supplied to the front and back compartments 6 and 7 and used for cleaning the sample 1 could be drawn directly into the drainage tank 17 through a piping 27 indicated by the dotted line in FIG. 2.

Figure 3:
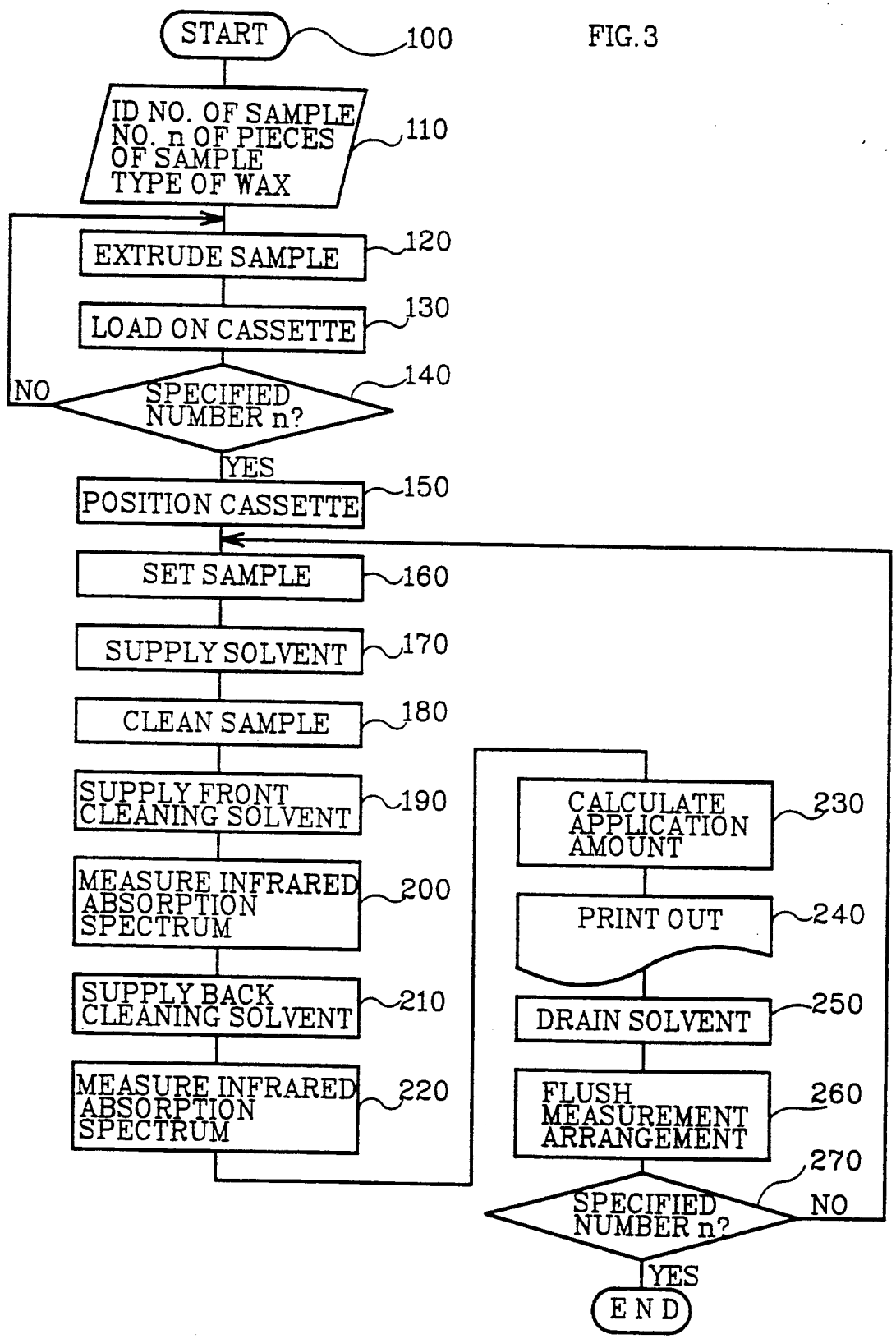
FIG. 3 is a flowchart showing measurement process steps using the automatic measuring device in FIG. 2.

A measuring operation using the measuring arrangement in FIG. 2 will now be explained with reference to the flowchart of FIG. 3. The computer 18 automatically carries out the process steps in the flowchart according to techniques well known to those skilled in the computer art which form no part of the present invention per se.

After starting the measuring operation at step 100, at step 110 the identification number of the sample 1, the number n of pieces of the sample 1 to be measured, the type of the wax applied over the sample 1, and other data are fed with the keyboard 20 into the computer 18. When automatic measuring starts in response to a control signal from the computer 18, at step 120 the sample 1 is punched from the paint-coated plate with wax applied thereon into a disc shape, for example. At step 130 the robot 3 confirms the front and back surfaces of the sample 1 and loads the sample 1 properly on the cassette 4. The front and back surfaces of the sample 1 are checked by detecting the reflectance of the coated portion on the front and back surfaces of the sample 1 with a photo sensor (not shown) on the robot 3, for example. Step 140 determines whether the robot 3 repeats the checking of the front and back surfaces of the sample 1 and the loading of the sample 1 the specified number n of times or not. After it is thus confirmed that the specified number n of pieces of the samples 1 have been loaded on the cassette 4, at step 150 the robot 3 conveys and positions the cassette 4 in place.

Subsequently, at step 160 the robot 3 detaches the first piece of the sample 1 from the cassette 4 and sets the first piece into the automatic cleaning cell 5. Specifically, the pair of cells 5a and 5b of the automatic cleaning cell 5 are separated, i.e. moved away from one another toward left and right, respectively, as FIG. 2 is viewed. The robot 3 inserts the sample 1 between the separated cells 5a and 5b, and the sample 1 is held therebetween. The robot 3 is then moved away from the pair of the cells 5a and 5b. Then, the cells 5a and 5b are closed and the sample 1 is thus held securely between them. An O-ring (not shown) is provided around the position where the pair of the cells 5a and 5b contact the sample 1 thus precisely defining an area on each side of the sample 1. The sample 1 is thus set in position, and the sample 1 and the hollows 5c and 5d of the cells 5a and 5b form the front and back compartments 6 and 7 sealed at the opposite sides of the sample 1.

Subsequently, the valves 13a and 13b are opened while the valves 14a and 14b are closed. The constant flow pump 12 is operated for a specified time period to draw up a specified amount of solvent such as carbon tetrachloride, hexane and other appropriate organic solvent from the solvent tank 9. At step 170, the solvent is thus supplied to the front and back compartments 6 and 7. When the solvent starts to be supplied, air in the piping 8 and the front and back compartments 6 and 7 is exhausted outside by the air regulating mechanism of the valves 13a and 13b.

By using the solvent supplied as aforementioned, at step 180 the front and back surfaces of the sample 1 are cleaned separately in the front and back compartments 6 and 7 of the automatic cleaning cell 5, respectively. The sample 1 is cleaned by rotating a rotor (not shown) in the front and back compartments 6 and 7 and stirring the solvent in the front and back compartments 6 and 7 with a magnetic force caused by the rotor in a manner well known to those skilled in the measuring instrument art.

At step 180, front and back cleaning solvents are thus obtained. Subsequently, at step 190 the valve 14a is opened and the front cleaning solvent is supplied from the front compartment 6 via the piping 10 into the flow cell 15 of the infrared spectroscope 11. For example, by using the suction of a pump (not shown) on the piping 16, the solvent can be forced from the front compartment 6 into the flow cell 15. At the same time, the air regulating mechanism of the valve 13a forces air into the front compartment 6.

At step 200, the emitting section 15a of the infrared spectroscope 11 emits an infrared ray into the front cleaning solvent supplied to the flow cell 15 and the detecting section 15b of the infrared spectroscope 11 measures the infrared absorption spectrum of the front cleaning solvent. After measuring, the front cleaning solvent in the flow cell 15 is drained to the drainage tank 17 by the operation of the pump of the piping 16.

In the same way as the front cleaning solvent, at step 210 the valve 14a is closed, the valve 14b is opened, and the back cleaning solvent is supplied from the back compartment 7 via the piping 10 into the flow cell 15 of the infrared spectroscope 11. At step 220, the emitting section 15a of the infrared spectroscope 11 emits an infrared ray to the back cleaning solvent supplied to the flow cell 15 and the detecting section 15b of the infrared spectroscope 11 measures the infrared absorption spectrum of the back cleaning solvent.

After the infrared absorption spectrum of the front and back cleaning solvents is measured, data signals reflecting the measurements taken are transmitted to the computer 18. At step 230, the computer 18 calculates the application amount of wax based on the measured data of the infrared absorption spectrum. Specifically, from the measured data of the infrared absorption spectrum transmitted from the infrared spectroscope 11, the computer 18 selects the data in the absorption band determined according to the type of the wax fed into the computer 18 at step 110 and reads the absorbency of the data in the absorption band. Subsequently, the absorbency is compared with a calibration curve from calibration data pre-stored in the computer 18. Based on the comparison results, the application amount of the wax over the front and back surfaces of the sample 1 is calculated according to well known mathematical techniques which will not be explained in detail in the interest of simplicity and the avoidance of redundancy. Alternatively, the computer 18 could calculate the application amount of the wax over the front surface of the sample 1 immediately after the infrared absorption spectrum of the front cleaning solvent is measured at step 200.

After the application amount is calculated, at step 240 the printer 21 or a plotter (not shown) prints out calculation result. At the same time, the calculation result is transmitted to the host computer 18a to be fed back to manufacturing process steps of the paint-coated plate.

After the measurement of the first piece of the sample 1 is finished, at step 250 remaining solvent in the flow cell 15 is drained via the piping 16 and associated components to the drainage tank 17. Subsequently, by following the procedure for setting the sample 1 into the automatic cleaning cell 5 in reverse order, the sample 1 is removed from the automatic cleaning cell 5, the pair of the cells 5a and 5b are closed, and the hollows 5c and 5d of the cells 5a and 5b form a sealed compartment. Subsequently, the constant flow pump 12 is operated, the valves 13a, 13b, 14a and 14b are fully opened, new solvent is supplied from the solvent tank 9 through the measurement arrangement. Specifically, at step 260 the measurement arrangement including the piping 8, the automatic cleaning cell 5 composed of the front and back compartments 6 and 7, the piping 10, the flow cell 15, the piping 16, the drainage tank 17 and associated components are flushed with the new solvent.

After the measurement apparatus has been flushed, step 270 determines whether the specified number n of pieces of the sample 1 have been measured. If step 270 determines that the specified number n of the pieces have not been measured yet, the process step goes back to step 160. The process steps from step 160 through step 260 are repeated until step 270 determines that the specified number n of the pieces have been measured, thereby ending the process steps at step 280.

In the preferred embodiment as shown, the computer 18 controls steps 120 through 280 and fully automates the measuring operation; however, steps 120 through 140 involving the punching out of the sample 1 and the loading of the sample 1 on the cassette 4 could be manually carried out, because the operator is not exposed to the solvent during these process steps. Further in the preferred embodiment as shown, after the specified number n of the pieces of the sample 1 have been loaded on the cassette 4, the samples 1 are set into the automatic cleaning cell 5 piece by piece. Without using the cassette 4, however, the sample 1 punched by the press 2 could be sequentially and continuously set into the automatic cleaning cell 5.

Also in the embodiment as shown, at step 240 the measuring result is printed out for each piece of the sample 1; however, the printing out of the measurement result could be done after the measurement of all the pieces of the sample 1 in one lot or the specified number n of the pieces of the sample 1 is finished. The measurement result of each piece of the sample 1 could be printed out. The average, the standard deviation or other values could be calculated and printed out based on the measurement result of each piece of the sample 1.

In the preferred embodiment, at step 110 the type of wax is manually fed into the computer 18; however, the computer 18 could store beforehand the waveform data of absorption spectrum and other data according to the type of wax. The data stored beforehand in the computer 18 could be compared with actually measured absorption spectrum to identify the type of wax automatically.

Typical measurement results will now be explained referring to the graphs of FIGS. 4 and 5. FIG. 4 shows the measurement result of the preferred embodiment as described above while FIG. 5 shows the measurement results of the prior art approach of quantitative analysis of sample pieces of one lot. In the graphs, the horizontal axis shows the number of the sample pieces and the longitudinal axis shows the application amount of wax over the sample pieces.

As clearly shown in FIGS. 4 and 5, the deviation of the measurement results provided by the present invention is between one seventh and one eighth of the deviation of the measurement results of the prior art manual measuring approach using quantitative analysis. In the data of FIG. 4, ten pieces of the sample were measured for twenty-four minutes, i.e. 2.4 minutes per sample piece, while in the prior art approach of FIG. 5, ten pieces of the sample were measured for ninety minutes, i.e. 9 minutes per sample piece. The time period required for the measuring operation with the present invention was one fourth of the time period required for the prior art quantitative analysis approach.

In the preferred embodiment of the present invention as described above, the sample 1 is punched from the paint-coated plate with wax applied thereon by the press 2 to form a specified configuration. The robot 3 automatically sets the sample 1 into the automatic cleaning cell 5. The front and back surfaces of the sample 1 are automatically cleaned, respectively, in the automatic cleaning cell 5 by using the solvent. The front and back cleaning solvents with wax dissolved therein are automatically fed into the infrared spectroscope 11. The infrared absorption spectrum of each of the front and back cleaning solvents is automatically measured. From the data of the infrared absorption spectrum measured by the spectroscope 11, the computer 18 reads the absorbency in the absorption band determined by the type of wax manually fed into the computer 18 or identified automatically by the computer 18. The absorbency is compared with the calibration curve stored beforehand in the computer 18, and the application amount of the wax over each of the front and back surfaces of the sample 1 is calculated automatically. With this invention, the application amount of wax can be measured automatically, thereby saving manual operations required for the measuring operation. The time period required for the measuring operation is also greatly reduced. As best seen in the graphs of FIG. 4, the measuring precision is similarly greatly enhanced.

By measuring the amount of wax over each of the front and back surfaces of the sample 1, the front and back surfaces of the paint-coated plate material of the sample 1 can also be distinguished. The reduction in time period for the measuring operation accelerates the feed back of the measuring result to the manufacturing process steps, thereby minimizing the occurrence of defective products. The reduction of the time period, the covering 22 around the measuring arrangement, and other advantageous features of this invention can also minimize the exposure of an operator to organic solvents and improve the safety and hygiene of the operator.

This invention has been described above with reference to a preferred embodiment as shown in the drawings. Modifications and alterations may become apparent to one skilled in the art upon reading and understanding the specification. Despite the use of a single embodiment for illustration purposes, however, it is intended to include all such modifications and alterations within the scope and spirit of the appended claims.

In this spirit, it should also be noted that in the embodiment as shown and described, the amount of the wax applied over the coated surface of the paint-coated plate is measured. However, wax, rust-preventive oil, press oil and other substances applied onto the surface of a plate other than the paint-coated plate could be measured.

In the embodiment as shown and described, the infrared absorption spectrum is measured a the absorption spectrum of the solvent; however, the ultraviolet absorption spectrum or another appropriate absorption spectrum could be measured instead. Additionally, the infrared spectroscope 11 measures the absorption spectrum, and the computer 18 computes the application amount. The infrared spectroscope 11, however, could be structured to both measure the absorption spectrum and compute the application amount.

Wherefore, having thus described the present invention, what is claimed is:

1. Automatic measuring apparatus for measuring an amount of a substance applied on a surface of a sample, comprising:
   a) cleaning means for cleaning a pre-established portion of the sample disposed in the cleaning means using a predetermined amount of a solvent and for dissolving the substance applied over said portion of the sample into said solvent;
   b) measuring means connected to said cleaning means for measuring an absorption spectrum of said solvent;
   c) calculating means connected to said measuring means for comparing data of said absorption spectrum measured by said measuring means and a pre-determined calibration data and for calculating an application amount of the substance over the sample based on results of said comparison; and,
   d) automatic control means for controlling said cleaning means, said measuring means and said calculating means, so that said cleaning means cleans a sample disposed in said cleaning means with a predetermined amount of said solvent, said solvent in said cleaning means is supplied to said measuring means after said cleaning means cleans said sample, said measuring means measures an absorption spectrum of said solvent, and said calculating means calculates an application amount of the substance based on data of said absorption spectrum measured by said measuring means.

2. The automatic measuring apparatus according to claim 1 wherein:
   said cleaning means includes an automatic cleaning cell comprising a pair of cells each having a hollow therein whereby said hollow of respective ones of said cells in combination with a sample disposed in said automatic cleaning cell form front and back compartments on opposite sides of said sample.

3. The automatic measuring apparatus according to claim 2 wherein additionally:
   said pair of cells are movable towards and away from one another whereby said sample can be inserted into and be removed from said automatic cleaning cell.

4. The automatic measuring apparatus according to claim 3 wherein:
   said automatic control means cleans front and back surfaces of said sample separately in said front and back compartments of said automatic cleaning cell, respectively, using said solvent.

5. The automatic measuring apparatus according to claim 4 wherein:
   a) said measuring means includes a flow cell, a light emitting section, and a detecting section;
   b) said emitting section emits infrared rays to cleaning solvent of said cleaning means supplied to said flow cell; and,
   c) said detecting section measures an infrared absorption spectrum of said cleaning solvent.

6. The automatic measuring apparatus according to claim 3 wherein:
   a) said automatic control means opens one of said outlet valves and supplies cleaning solvent from said front compartment via said outlet piping into a flow cell of an infrared spectroscope by using suction on a drainage piping and forces said solvent from each compartment into said flow cell; and, valves having an air regulating mechanism which forces air into said front compartment.

7. The automatic measuring apparatus according to claim 2 wherein said cleaning means additionally comprises:
   a) an inlet piping;
   b) an outlet piping;
   c) a solvent tank;
   d) a constant flow pump;
   e) a pair of inlet valves having an air regulating mechanism; and,
   f) a pair of outlet valves; wherein,
   g) said front and back compartments are each connected at one end through said inlet piping to said solvent tank and at another end connected through said outlet piping to said measuring means;
   h) said automatic control means controls said inlet valves to open while said outlet valves close and controls said constant flow pump to operate for a pre-established time period to draw up a pre-established amount of said solvent, and when said solvent starts to be supplied to said front and back compartments, air in said inlet piping and said front and back compartments is exhausted outside by said air regulating mechanism of said inlet valves.

8. The automatic measuring apparatus according to claim 7, wherein:
   a) said constant flow pump is connected in line with said inlet piping;
   b) said inlet piping is connected via said inlet valves to a respective solvent inlet of a said compartment of said automatic cleaning cell;
   c) said outlet piping is connected from a respective solvent outlet of a said compartment via said outlet valves to said measuring means.

9. The automatic measuring apparatus according to claim 2 additionally including a robot and a cassette and wherein said automatic control means includes means:
   a) for causing said robot to load a sample on said cassette;
   b) for causing said robot to convey said cassette to said automatic cleaning cell, to detach a piece of said sample from said cassette and to set said piece into said automatic cleaning cell;
   c) for separating said pair of said cells of said automatic cleaning cell;
   d) for inserting said piece of said sample between said separated cells;
   e) for holding said piece of said sample properly between said separated cells;
   f) for moving said robot away from said pair of said cells; and,
   g) for closing said cells whereby said piece of said sample is thus held securely.

10. The automatic measuring apparatus according to claim 2 wherein:
   a) front and back cleaning solvents with the substance dissolved therein are automatically fed into an infrared spectroscope;
   b) an infrared absorption spectrum of each of said front and back cleaning solvents is automatically measured;
   c) from data of said infrared absorption spectrum measured by said spectroscope said calculating means reads absorbency in an absorption band determined by a type designator associated with the substance;
   d) said absorbency is compared with a calibration curve stored beforehand in said calculating means; and,
   e) an application amount of the substance over each of said front and back surfaces of the sample is calculated automatically as a function of comparison data between said absorbency and said calibration curve.

11. The automatic measuring apparatus according to claim 1, wherein:
   said measuring means includes an infrared spectroscope having a flow cell, a light emitting section, and a detecting section.

12. The automatic measuring apparatus according to claim 11 wherein:
   said infrared spectroscope is a Fourier-transform infrared spectroscope.

13. The automatic measuring apparatus according to claim 11 wherein:
   a) said measuring means includes a drainage piping and a drainage tank;
   b) said flow cell is at an inlet connected to said cleaning means through an outlet piping of said cleaning means;
   c) said flow cell is at an outlet connected through said drainage piping to said drainage tank; and wherein,
   d) after measurement of said sample is finished, said automatic control means drains remaining solvent in said flow cell via said drainage piping to said drainage tank.

14. The automatic measuring apparatus according to claim 11 wherein:
   a) said emitting section of said infrared spectroscope emits infrared rays to each cleaning solvent supplied to said flow cell; and,
   b) said detecting section of said infrared spectroscope measures an infrared absorption spectrum of each said cleaning solvent.

15. The automatic measuring apparatus according to claim 11 wherein:
   a) said infrared spectroscope is connected to said calculating means and said automatic control means; and,
   b) said calculating means is connected to a display, a keyboard, a printer, and a host computer.

16. The automatic measuring apparatus according to claim 15 wherein:
   said calculating means compares absorbency with a calibration curve as calibration data stored in said calculating means and separately calculates, based on comparison results, an application amount of the substance over front and back surfaces of the sample.

17. The automatic measuring apparatus according to claim 15 wherein:
   after an application amount is calculated, said calculating means causes said printer to print out a calculation result and said calculation result to be transmitted to said host computer to be fed back to manufacturing process control steps of a paint-coated plate.

18. The automatic measuring apparatus according to claim 15 wherein:
   said calculating means causes said printer to print out a measurement result of each piece of the sample, and calculates and causes said printer to print out an average and a standard deviation based on said measurement result of each piece of the sample.

19. The automatic measuring apparatus according to claim 7 wherein:
   said infrared spectroscope both measures said absorption spectrum and computes said application amount.

20. The automatic measuring apparatus according to claim 11 wherein:
   a) said calculating means calculates an application amount of the substance based on measured data of said infrared absorption spectrum transmitted from said infrared spectroscope; and,
   b) said calculation means selects data in an absorption band determined according to a type designation of the substance fed into said calculating means and reads absorbency of said data in said absorption band.

21. The automatic measuring apparatus according to claim 1 wherein:
   said solvent is selected from a group consisting of carbon tetrachloride, hexane and organic solvents.

22. The automatic measuring apparatus according to claim 1 wherein:
   said measuring means measures an application amount of the substance which is selected from a group consisting of wax, rust-preventive oil, and press oil applied onto a surface of a paint-coated plate as the sample.

23. The automatic measuring apparatus according to claim 1 wherein:
   said measuring means measures an ultraviolet absorption spectrum.

24. The automatic measuring apparatus according to claim 1 wherein:
   a) said calculating means stores beforehand waveform data of absorption spectrum according to a type designation of the substance; and,
   b) said calculating means compares waveform data stored beforehand with actually measured absorption spectrum data to identify a type of the substance automatically.

* * * * *

UNITED STATES PATENT AND TRADEMARK OFFICE
CERTIFICATE OF CORRECTION

PATENT NO. : 5,132,919

DATED : July 21, 1992

INVENTOR(S) : Masahiro NISHIO et al

It is certified that error appears in the above-identified patent and that said Letters Patent is hereby corrected as shown below:

Column 10, line 30 change "claim 7" to --claim 11--.

Signed and Sealed this

Fifth Day of October, 1993

Attest:

BRUCE LEHMAN

Attesting Officer     Commissioner of Patents and Trademarks